(12) United States Patent
Vrancken Peeters

(10) Patent No.: US 12,256,924 B2
(45) Date of Patent: Mar. 25, 2025

(54) NEEDLE-SUTURE COMBINATION, NEEDLE HOLDER AND SURGICAL SUTURE APPARATUS

(71) Applicant: Mellon Medical B.V., The Hague (NL)

(72) Inventor: Mark-Paul Franciscus Maria Vrancken Peeters, The Hague (NL)

(73) Assignee: Mellon Medical B.V., The Hague (NL)

( * ) Notice: Subject to any disclaimer, the term of this patent is extended or adjusted under 35 U.S.C. 154(b) by 1138 days.

(21) Appl. No.: 17/049,358

(22) PCT Filed: Apr. 25, 2019

(86) PCT No.: PCT/NL2019/050242
§ 371 (c)(1),
(2) Date: Oct. 21, 2020

(87) PCT Pub. No.: WO2019/209108
PCT Pub. Date: Oct. 31, 2019

(65) Prior Publication Data
US 2021/0236118 A1 Aug. 5, 2021

(30) Foreign Application Priority Data
Apr. 25, 2018 (NL) ..................................... 2020824

(51) Int. Cl.
*A61B 17/062* (2006.01)
*A61B 17/06* (2006.01)

(52) U.S. Cl.
CPC .... *A61B 17/0625* (2013.01); *A61B 17/06004* (2013.01); *A61B 17/06066* (2013.01);
(Continued)

(58) Field of Classification Search
CPC .......... A61B 17/0625; A61B 17/06004; A61B 17/06066; A61B 2017/06019; A61B 2017/0609
See application file for complete search history.

(56) References Cited

U.S. PATENT DOCUMENTS 5,690,652 A 11/1997 Wurster et al.
2015/0230790 A1 8/2015 Hashimoto
(Continued)

FOREIGN PATENT DOCUMENTS

EP 2 889 008 A1 7/2015
EP 3 175 798 A1 6/2017
(Continued)

OTHER PUBLICATIONS

Japanese Office Action Dated Apr. 4, 2023 for counterpart foreign application.

*Primary Examiner* — Ashley L Fishback
(74) *Attorney, Agent, or Firm* — Hoffmann & Baron, LLP

(57) ABSTRACT

A needle-suture combination includes a needle having a first needle end and a second needle end opposite to the first needle end, and a suture connected to the needle between the first needle end and the second needle end. Each of the first needle end and the second needle end includes a needle point and a locking groove to receive a locking element of a needle holder. The first needle end and the second needle end each include a needle end stop surface between the groove and the needle point, where the needle end stop surface is arranged to cooperate with a needle channel stop surface of a needle channel of a needle holder.

12 Claims, 6 Drawing Sheets

(52) U.S. Cl.
CPC ............... *A61B 2017/06019* (2013.01); *A61B 2017/0609* (2013.01)

(56) References Cited

U.S. PATENT DOCUMENTS

| | | |
|---|---|---|
| 2017/0086819 A1 | 3/2017 | Raybin et al. |
| 2017/0150961 A1 | 6/2017 | Marczyk et al. |

FOREIGN PATENT DOCUMENTS

| | | |
|---|---|---|
| ER | 0 107 961 A1 | 5/1984 |
| ES | 2 366 248 T3 | 10/2011 |
| JP | S59-95038 A | 5/1984 |
| WO | 2014/030544 A1 | 2/2014 |
| WO | 2015/167331 A1 | 11/2015 |
| WO | 2017/155406 A1 | 9/2017 |

NEEDLE-SUTURE COMBINATION, NEEDLE HOLDER AND SURGICAL SUTURE APPARATUS

CROSS-REFERENCE TO RELATED APPLICATIONS

This application is the National Stage of International Application No. PCT/NL2019/050242, filed Apr. 25, 2019, which claims the benefit of Netherlands Application No. 2020824, filed Apr. 25, 2018, the contents of which is incorporated by reference herein.

FIELD OF THE INVENTION

The present invention relates to a needle-suture combination, a needle holder to cooperate with such needle-suture combination and a surgical suture apparatus incorporating the needle holder.

BACKGROUND OF THE INVENTION

A surgical suture apparatus for passing a double-ended surgical needle of a needle-suture combination forwards and backwards is known from prior art.

An example of such surgical apparatus is known from WO 2017/155406, the contents of which is herein incorporated by reference, in its entirety.

This known surgical apparatus comprises a first jaw element and a second jaw element. The first jaw element comprising a first needle holder to hold a first needle end of the surgical needle-suture combination, and the second jaw element comprises a second needle holder to hold a second needle end of the surgical needle-suture combination.

An operating device is provided, to operate the first needle holder and the second needle holder to alternately hold the first needle end by the first needle holder and the second needle end by the second needle holder.

The first jaw element and the second jaw element are movable with respect to each other between a take-over position, wherein a surgical needle can be passed between the first needle holder and the second needle holder, and an open position, wherein the first needle holder and the second needle holder are spaced further from each other.

In the surgical apparatus of WO 2017/155406, the first jaw element and the second jaw element are moved, to activate the operating device, from the take-over position towards each other. This activation movement of the first jaw element and the second jaw element from the take-over position towards each other takes particularly place at the parts of the first jaw element and the second jaw element, where operating surfaces or operating elements are provided to exert a pinching force on the first jaw element and the second jaw element. These operating surfaces or operating elements are for example provided in a middle part of the first jaw element and the second jaw element, i.e. between the distal end and the proximal end of the first jaw element and the second jaw element, respectively.

To allow this activation movement, the first jaw element and/or the second jaw element may be bendable. As an alternative, the first jaw element and/or the second jaw element may be provided with a rotation point within the respective jaw element for rotation of a first jaw part with respect to a second jaw part. By this bending or internal rotation of the first jaw element and/or the second jaw element, the first jaw element and the second jaw element can be moved towards each other in a middle part thereof, while the proximal ends and the distal ends of the first jaw element and the second jaw element remain substantially in the same position.

At the beginning of the activation movement, the first jaw element and the second jaw element are in the take-over position, in which the needle ends of the needle-suture combination are already placed in the first needle holder and the second needle holder. Therefore, the first jaw element and the second jaw element are configured to rotate about the respective needle points of the needle ends arranged in the first needle holder and the second needle holder during the activation movement of the first jaw element and the second jaw element.

A drawback of this configuration of the surgical suture apparatus, and in particular of the activation movement of the first jaw element and the second jaw element, is that the rotation of the first jaw element and the second jaw element about the respective needle points of the needle ends may have a negative effect on the shape and/or condition of the needle ends.

SUMMARY OF THE INVENTION

It is an aim of the present invention, to provide a needle-suture combination and/or a needle holder that facilitates the use of a needle-suture combination in a surgical suture apparatus of the type as described above. Generally, it is an aim of the invention to provide an improved needle-suture combination and/or needle holder for a surgical suture apparatus, in particular a surgical suture apparatus as disclosed in WO 2017/155406.

The present invention provides a needle-suture combination as described herein.

The needle-suture combination comprises a needle and a suture connected to the needle. The suture is connected to the needle between the first needle end and the second needle end. The needle has a first needle end and a second needle end, opposite to the first needle end. Each of the first needle end and the second needle end comprises a needle point and a locking groove to receive a locking element of a needle holder.

In accordance with the invention, the first needle end and the second needle end each comprise a needle end stop surface between the locking groove and the needle point, wherein the needle end stop surface is arranged to cooperate with a needle channel stop surface of a needle channel of a needle holder. By providing a specific needle end stop surface on the needle, separate from the needle point, to cooperate with the needle channel stop surface of a needle holder, the contact between the needle end stop surface and the needle channel stop surface can be optimized for rotation of the first jaw element and the second jaw element about the respective needle ends. Furthermore, the needle point itself does not have to be in contact with the needle channel, thereby avoiding damage to the needle point.

The needle end stop surface may be optimized for the rotation of the needle end stop surface with respect to the needle channel stop surface. For example, the shape of the needle end stop surface may be adapted for this reason, for example the needle end stop surface may be hardened.

The needle end stop surface may be coated, for example with a lubricating coating that facilitates movement of the needle end stop surface over the needle channel stop surface or with a wear-resistant coating that reduces wear of the needle end stop surface.

Since the needle end stop surface is arranged to provide a contact between the needle and the needle channel to facilitate the rotation of the first jaw element and the second jaw element about the respective needle ends, the needle point is no longer needed to provide an engagement between the needle and the needle channel. As a result, the needle point of each of the first needle end and the second needle end may be optimized for piercing of tissue.

In an embodiment, each needle point comprises a needle point surface extending at a first acute angle with respect to a longitudinal axis of the needle, wherein each needle end stop surface extends at a second acute angle with respect to the longitudinal axis of the needle, and wherein the first acute angle is larger than the second acute angle.

The needle point surface is the surface or the surfaces that define(s) the needle point.

It has been found that it is advantageous for rotation of the first jaw element and the second jaw element about the needle ends that the needle end stop surface is more parallel to the longitudinal axis of the needle than the needle point surface of the needle point. Since the needle end stop surface is separate from the needle point, the angle of the needle end stop surface can be made more parallel to the longitudinal axis of the needle, while the angle of the needle point surface of the needle can be provided at a larger angle with respect to the longitudinal axis of the needle.

In an embodiment, the needle point surface may be arranged at a first acute angle in the range of 15 to 40 degrees with respect to the longitudinal axis of the needle, for example in the range of 20 to 30 degrees with respect to the longitudinal axis of the needle.

In an embodiment, the needle end stop surface may be arranged at a second acute angle in the range of 5 to 20 degrees with respect to the longitudinal axis of the needle, for example in the range of 8 to 15 degrees with respect to the longitudinal axis of the needle.

In an embodiment, the needle point surface of the needle point is at least partially conical. The needle point surface of the needle point of each needle end may have a substantially conical shape ending in a sharp point. The needle point surface may also have any other suitable shape, for example three facets ending in a sharp point.

In an embodiment, the needle end stop surface is at least partially conical. The needle end stop surface of each needle end may be substantially conical. It has been found that a conical surface is suitable as a rotation surface for the first jaw element and the second jaw element. Furthermore, a conical shape of the needle end stop surface allows the needle to be placed in any rotational position in the needle channel while maintaining a proper engagement between the needle end stop surface and the needle channel stop surface. The needle end stop surface may also have any other suitable shape, for example a spherical shape. Generally, the needle end stop surface will have a surface that is at a non-zero angle with respect to the longitudinal axis of the needle. The needle end stop surface may be symmetric with respect to the longitudinal axis of the needle.

In an embodiment, the substantially conical needle end stop surface is slightly convex. Slightly convex means that the main shape of the needle end stop surface is substantially conical, but that in this main conical shape the surface is convex. Such convex shape may improve the rotation of the first jaw element and the second jaw element about the needle ends of the needle.

In an embodiment, the needle is a straight needle. The advantage of a straight needle, in particular when the needle has a small diameter, is that the needle is more suitable to withstand the longitudinal compression force resulting of pushing the first jaw element and the second jaw element towards each other on the needle ends. Furthermore, a straight needle can be arranged in the needle channels independent of its rotational position.

In an embodiment, the locking groove extends around a complete circumference of the needle. By providing a straight needle and a circumferential locking groove, the needle can properly be arranged in the needle channel of a surgical suturing apparatus, independent of the rotational position of the needle. This is advantageous, as it is no longer required to align the rotational position of the needle with respect to the needle channel before loading the needle into the needle holder. When a needle is to be reloaded, for example after temporarily release from the needle holder, it is less difficult to reload the needle into a needle holder, since the user does not have to adapt the rotational position of the needle to reload the needle into the needle holder.

Another advantage of the needle being independent of the rotational position, is that the needle will be arranged in different rotational positions in the needle holders, which reduces wear at a specific location.

The invention further provides a needle holder to hold a needle-suture combination, wherein the needle holder comprises:
  a needle channel arranged to receive the first needle end or the second needle end, the needle channel comprising an inlet to introduce the respective needle end into the needle channel, and
  a needle locking element to lock the respective needle end in the needle channel,
  wherein the needle channel comprises a needle channel stop surface to cooperate with a needle end stop surface of the needle-suture combination.

The needle-suture combination of the invention can advantageously be used in a needle holder, in particular a needle holder having a needle channel provided with a needle channel stop surface designed to cooperate with the respective stop surface of the needle end. The needle end stop surface and the needle channel stop surface may be substantially mating surfaces.

The needle end stop surface and the needle channel stop surface cooperate with each other to form a bearing structure that allows movement of the needle channel stop surface with respect to the needle end stop surface to facilitate rotational movement of the first jaw element and the second jaw element of a surgical suture apparatus about the respective needle ends of the needle-suture combination.

The needle channel stop surface may be optimized for this rotation movement. For example, the shape of the needle channel stop surface may be adapted, for example the needle channel stop surface may be hardened.

The needle channel stop surface may be coated for example with a lubricating coating that facilitates movement of the needle end stop surface over the needle channel stop surface, or with a wear-resistant coating that reduces wear of the needle channel stop surface.

The locking element is movable between a locking position and a non-locking position. In the locking position, the locking element will extend into the locking groove of the needle end of a needle introduced into the needle channel, and in the non-locking position the locking element will be moved out of the needle channel such that the needle is free to move in and out of the needle channel.

In case the needle comprises circumferential locking grooves, the locking element can be moved in a direction radially with respect to the longitudinal axis of the needle channel and therefore radially with respect to the longitudinal axis of the needle arranged in the needle channel.

In an embodiment, the needle channel stop surface is substantially conical. The angle of the needle channel stop surface may substantially correspond with the angle of the needle end stop surface such that there is a contact plane instead of a contact line between the needle end stop surface and the needle channel stop surface of the needle channel. In another embodiment, the needle channel contact surface may have any other suitable shape, for example spherical to facilitate rotation of the jaw elements about the needle ends.

In an embodiment, the substantially conical needle channel stop surface is slightly concave. Slightly concave means that the main shape of the needle channel stop surface is substantially conical, but that in this main conical shape the surface is concave. Such concave shape may improve the rotation of the first jaw element and the second jaw element about the needle ends of the needle.

In an embodiment, the needle channel is configured to be free of contact of the needle point when the needle channel stop surface engages the needle end stop surface. Since the needle end stop surface and the needle channel stop surface are arranged to provide a contact plane between the needle and the needle holder, the needle point no longer has to be in direct contact with the needle channel surface when the needle is arranged in the needle channel. This means that the needle point cannot be damaged by contact between the needle channel and the needle, when the needle is arranged in the needle channel.

In an embodiment, the needle channel comprises at the inlet an alignment funnel to align the needle end with the needle channel. To allow rotation of the jaw elements with respect to the needle ends, some play of the longitudinal axis of the needle with respect to the longitudinal axis of the needle channel has to be provided. As a result, the needle may not always be perfectly aligned with the needle channel when the first jaw element and the second jaw element are moved from the open position, in which only one needle end is arranged in a needle channel of the respective needle holder, to the take-over position, in which both needle ends are arranged in the needle holders. To ensure that the needle end is properly introduced into the needle channel, an alignment funnel may be provided at the inlet of the needle channel. The alignment funnel is arranged to receive the needle end and guide it towards the needle channel, while aligning the longitudinal axis of the needle with the longitudinal axis of the needle channel. The alignment funnel will typically have a funnel surface, for example a substantially conical surface, that narrows towards the needle channel. The wide end of the alignment funnel may have a cross section having a diameter of at least two times the needle diameter, for example at least three times the needle diameter.

It is remarked that the alignment funnel may be used for the alignment of a needle of any surgical needle-suture combination. Therefore, there is also provided a needle holder to hold a surgical needle-suture combination, wherein the needle holder comprises a needle channel arranged to receive a needle end of a needle of the needle-suture combination, the needle channel comprising an inlet to introduce the respective needle end into the needle channel, wherein the needle channel comprises at the inlet an alignment funnel to align the needle end with the needle channel. Such needle holder may be provided in a surgical suture apparatus for passing a double-ended surgical needle-suture combination forwards and backwards, wherein the surgical apparatus comprises:

a first jaw element and a second jaw element, each comprising such needle holder, an operating device to operate the needle holders to alternately hold a first needle end by one of the needle holders and a second needle end by the other of the needle holders, wherein the first jaw element and the second jaw element are movable with respect to each other between a take-over position, in which the needle-suture combination can be passed between the needle holders, and an open position, in which the first needle holder and the second needle holder are spaced further from each other.

In an embodiment, the alignment funnel comprises a funnel surface at an acute funnel surface angle with respect to a longitudinal axis of the needle channel, wherein the acute funnel surface angle is substantially the same as or smaller than the first acute angle of the needle point surface of the needle point. By providing a funnel surface that is at a same or smaller angle than a needle point surface of the needle point, it is prevented that the needle point will pierce into the funnel surface when the needle end is pushed onto the funnel surface.

In an embodiment, the needle channel comprises a needle holding part having a first diameter and in which the needle channel stop surface is provided, and a tissue receipt channel part between the needle holding part and the inlet of the needle channel, the tissue receipt channel part having a second diameter, wherein the second diameter is larger than the first diameter.

It has been found that when the needle end is pierced through tissue and then brought into the needle channel, tissue may be pulled into the needle channel. When this tissue is pulled in the needle holding part of the needle channel, which typically has a diameter that is slightly larger than the needle, it may clamp or jam the needle and/or tissue in the needle channel resulting in tissue interposition. To avoid this from happening, or to at least reduce the risk that the needle is jammed or clamped in the needle channel due to tissue being pulled together with the needle end into the needle channel, the needle is provided with a tissue receipt channel part between the inlet and the needle holding part that has a larger diameter than the needle holding part. The second diameter of the tissue receipt channel part is selected such that there is a circumferential space around the needle in the tissue receipt channel part, in which tissue can be accommodated when being pulled into the needle channel.

The tissue receipt channel part should have sufficient length to avoid that the tissue pulled into the needle channel is pulled through the complete tissue receipt channel part and into the needle holding part, not only to prevent jamming or clamping of the needle but also to further reduce damage to the tissue.

In an embodiment, the length of the tissue receipt channel part is for example at least 1, for example at least 1.3 times, for instance at least 1.5 times the second diameter, i.e. the diameter of the tissue receipt channel part.

In an embodiment, the second diameter is in the range of 1.2 to 2.5 times the first diameter, for example in the range of 1.3 to 1.8 times the first diameter, for instance about 1.5 times the first diameter. It has been found that an increased diameter of the tissue receipt channel part is beneficial in order to accommodate tissue pulled into the needle channel. The diameter should not be too small in order to avoid that the tissue will clamp or jam the needle in the needle channel, but also not too large to avoid that a large volume of tissue is pulled into the needle channel.

The second diameter may decrease over the length of the tissue receipt channel part, from the inlet towards the needle holding part. In an embodiment, the second diameter of the tissue receipt channel part decreases in steps, as the steps in the second diameter may effectively stop the tissue from being pulled further into the needle channel.

It is remarked that a tissue receipt channel part may be used in the needle channel of any needle holder. Therefore, there is also provided a needle holder to hold a surgical needle-suture combination, wherein the needle holder comprises a needle channel arranged to receive a needle end of a needle of the needle-suture combination, the needle channel comprising: an inlet to introduce the respective needle end into the needle channel, a needle holding part having a first diameter, and a tissue receipt channel part between the needle holding part and the inlet of the needle channel, the tissue receipt channel part having a second diameter, wherein the second diameter is larger than the first diameter. Such needle holder may be provided in a surgical suture apparatus for passing a double-ended surgical needle-suture combination forwards and backwards, wherein the surgical apparatus comprises:
- a first jaw element and a second jaw element, each comprising such needle holder,
- an operating device to operate the needle holders to alternately hold a first needle end by one of the needle holders and a second needle end by the other of the needle holders, wherein the first jaw element and the second jaw element are movable with respect to each other between a take-over position, in which the needle-suture combination can be passed between the needle holders, and an open position, in which the first needle holder and the second needle holder are spaced further from each other.

The invention further provides a surgical suture apparatus for passing a double-ended surgical needle-suture combination forwards and backwards, wherein the surgical apparatus comprises:
- a first jaw element, comprising a first needle holder configured as the needle holder according to the present invention to hold a first needle end of the needle,
- a second jaw element comprising a second needle holder configured as the needle holder according to the present invention to hold a second needle end of the needle, and
- an operating device to operate the first needle holder and the second needle holder to alternately hold the first needle end by the first needle holder and the second needle end by the second needle holder.

As explained above, the needle-suture combination and the needle are advantageous to be used in a surgical suture apparatus. In particular, the provision of a combination of a needle end stop surface on the needle and a needle channel stop surface in the needle channel is advantageous in a surgical suture apparatus, in which the jaw elements bend or have internal rotation to move the jaw elements, partially, from the take-over position towards each other for activation of the operating device, such as disclosed in WO 2017/155406.

BRIEF DESCRIPTION OF THE DRAWINGS

Further characteristics and features of embodiments of the invention will be described hereinafter, whereby reference will be made to the accompanying drawings, in which.

DETAILED DESCRIPTION OF THE INVENTION

Figure 1:
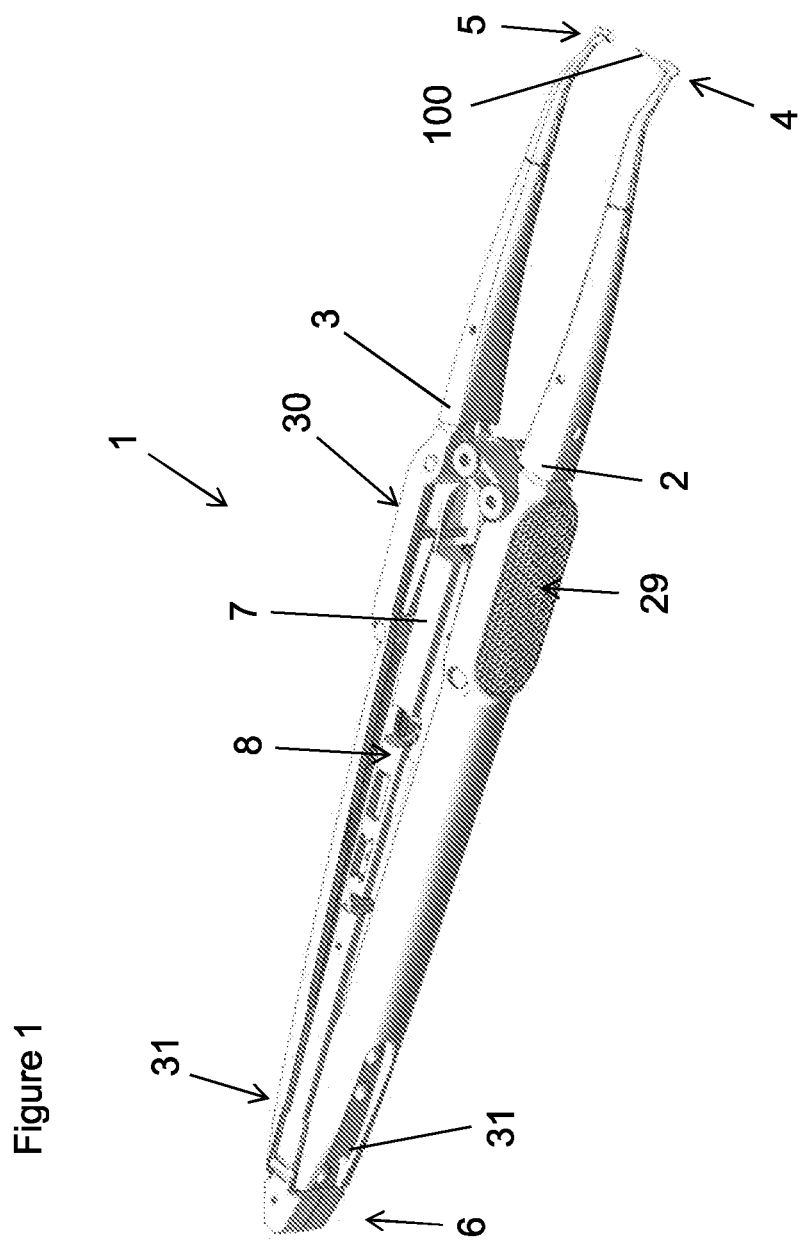
FIG. 1 shows a perspective view of an embodiment of a surgical suture apparatus according to the invention.
Figure 2:
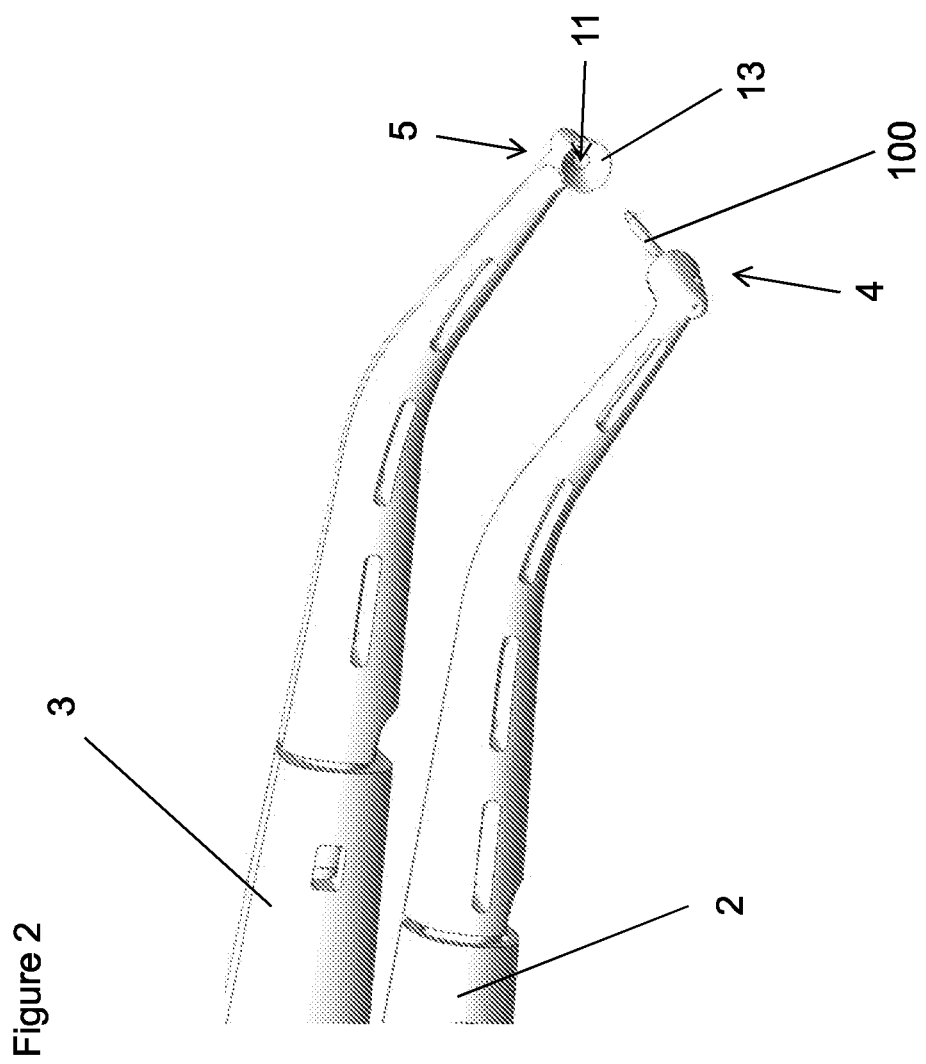
FIG. 2 shows the distal end of the embodiment of FIG. 1 in more detail.

FIG. 1 shows schematically an embodiment of a surgical apparatus of the invention. The surgical apparatus is generally indicated by reference numeral 1. FIG. 2 shows the distal end of the surgical apparatus in more detail.

The surgical apparatus 1 comprises a first jaw element 2 and a second jaw element 3. The first jaw element 2 comprises a first needle holder 4 configured to hold a needle end of a needle 100, and the second jaw element 3 comprises a second needle holder 5 configured to hold an opposite needle end of the needle 100.

The surgical apparatus 1 is configured to pass a double-ended surgical needle 100 forwards and backwards so that the surgical apparatus can be used to apply sutures to human or animal body tissue. The surgical apparatus 1 may be made of any suitable material such as a (non-toxic and/or biocompatible) plastic or metal, or combinations thereof.

The proximal ends of the first jaw element 2 and the second jaw element 3 are connected to each other at a proximal end 6 of the apparatus 1.

The first jaw element 2 and the second jaw element 3 are movable with respect to each other between a take-over position, in which the surgical needle 100 can be taken over between the first needle holder 4 and the second needle holder 5, and an open position, in which the first needle holder 4 and the second needle holder 5 are spaced further from each other. In FIG. 1, the surgical apparatus 1 is shown in the open position. In this open position, body tissue can be placed between the needle 100 and the one of the first jaw element 2 and the second jaw element 3 that does not hold the needle 100.

Between the first jaw element 2 and the second jaw element 3, a main body 7 of the surgical apparatus is provided. In this main body 7, an operating device 8 is arranged, which operating device 8 is configured to operate the first needle holder 4 and the second needle holder 5, to alternately hold the first needle end of the needle 100 by the first needle holder 4 and the second needle end by the second needle holder 5.

The surgical suture apparatus 1 may, unless otherwise described an/or shown in this patent application, be constructed as described and shown in WO 2017/155406, the contents of which is herein incorporated by reference, in its entirety.

FIG. 1 shows the suture apparatus 1 in the normal, non-actuated state of the apparatus. The first jaw element 2 and the second jaw element 3 are arranged in the open position. A first needle end of the needle 100 is held by the first needle holder 4 and the second needle holder 5 is spaced from the opposite second needle end. In this non-actuated position of the apparatus, the needle 100 can be pierced through body tissue to place a suture using a suture attached to the needle 100.

When the needle 100 is correctly placed through tissue, the first jaw element 2 and the second jaw element 3 may be moved from the open position to the take-over position, by exerting a pinching force, for example with a thumb and a finger on a first operating surface 29 on the first jaw element 2 and a second operating surface 30 on the second jaw element 3, respectively. In the take-over position, the first needle end is still held by the first needle holder 4, and the second needle end is arranged in the second needle holder 5.

In the take-over position, it can still be checked whether the needle 100 is correctly placed in the tissue. When correction of the placement of the needle is desired the pinching force on the first operating surface 29 and the second operating surface 30 can be released, and the first jaw element 2 and the second jaw element 3 will move back to the open position. When no correction of the placement of the needle 100 is desired, the operating device 8 can be activated to release the first needle end in the first needle holder 4 and simultaneously lock the second needle end in the second needle holder 5.

To activate the operating device 8, the first jaw element 2 and the second jaw element 3 can be moved in an activation movement from the take-over position towards each other. It is remarked that only the middle parts of the first jaw element 2 and the second jaw element 3, i.e. at the location of the first operating surface 29 and the second operating surface 30, will move towards each other during the activation movement, since the proximal ends of the first jaw element 2 and the second jaw element 3 are connected to each other, and the needle 100 prevents further movement of the distal ends of the first jaw element 2 and the second jaw element 3 towards each other.

This means that the needle 100 is used, during the activation movement, as a hinge for rotation of the first jaw element 2 and the second jaw element 3. Furthermore, the activation movement requires bending of the first jaw element 2 and the second jaw element 3 in order to move the first operating surface 29 and the second operating surface 30 towards each other. To facilitate bending of the first jaw element 2 and the second jaw element 3, the first jaw element 2 and the second jaw element 3 may be provided with flexible portions 31 (see FIG. 1) near the proximal end 6 of the apparatus 1, but the first jaw element 2 and the second jaw element 3 are also configured to bend over other parts of their extension to allow the first operating surface 29 and the second operating surface 30 to move from the take-over position towards each other.

When the first jaw element 2 and the second jaw element 3 are released, the first jaw element 2 and the second jaw element 3 will move back to the open position as shown in FIG. 1, but the needle is now held by the second needle holder 5.

When the first jaw element 2 and the second jaw element 3 are now again moved from the open position to the take-over position, and subsequently at least partly further towards each other in the activation movement, the operating device 8 will again be activated to release the second needle end in the second needle holder 5 and simultaneously lock the first needle end in the first needle holder 4.

It will be clear that by subsequent further actuation of the apparatus 1, the needle can be passed forwards and backwards between the first needle holder 4 and the second needle holder 5 to apply a suture through the tissue.

Figure 3:
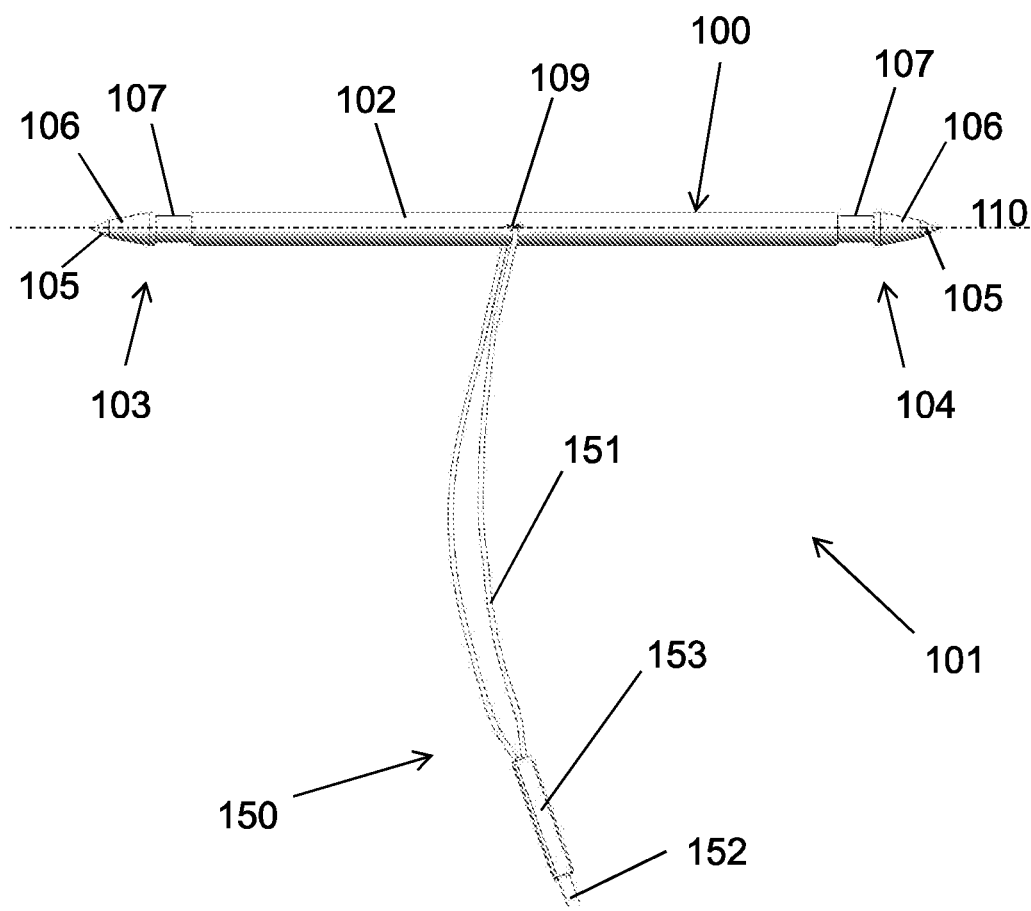
FIG. 3 shows an embodiment of a needle-suture combination according to an embodiment of the invention.

FIG. 3 shows a needle-suture combination 101 according to the embodiment of the invention that is configured to be used in the embodiment of the surgical apparatus of FIGS. 1 and 2.

The needle-suture combination 101 comprises a needle 100 and a suture 150. The suture 150 comprises a connection loop 151, a suture thread 152, only partly shown, and a connector 153 connecting the suture thread 152 to the connection loop 151. The connection loop 151 is made of a wire or thread having a smaller diameter than the suture thread 152.

The needle 100 comprises a straight needle body 102 having a first needle end 103 and a second needle end 104. Midway between the first needle end 103 and the second needle end 104, a through-going hole 109 is provided through which the connection loop 151 of the suture 150 is arranged to connect the suture 150 to the needle 100.

Each of the first needle end 103 and the second needle end 104 comprises a needle point 105, a needle end stop surface 106 and a circumferential locking groove 107.

The needle point 105 is a pointed end of the needle 100 that can be used to pierce tissue or other material through which the suture 150 should be arranged.

Figure 5:
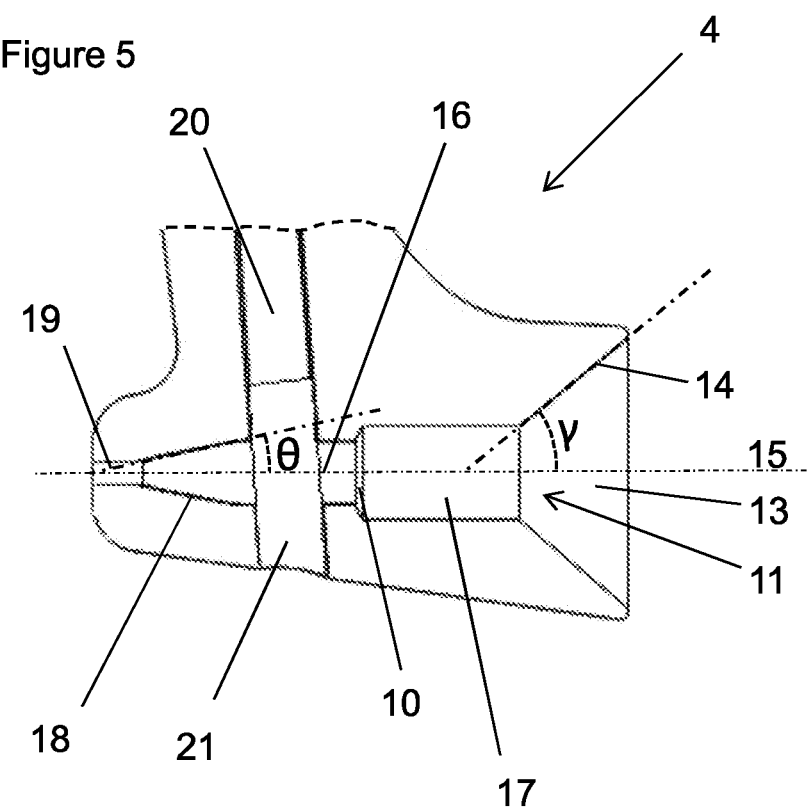
FIG. 5 shows a cross section of a needle holder according to an embodiment of the invention.
Figure 6:
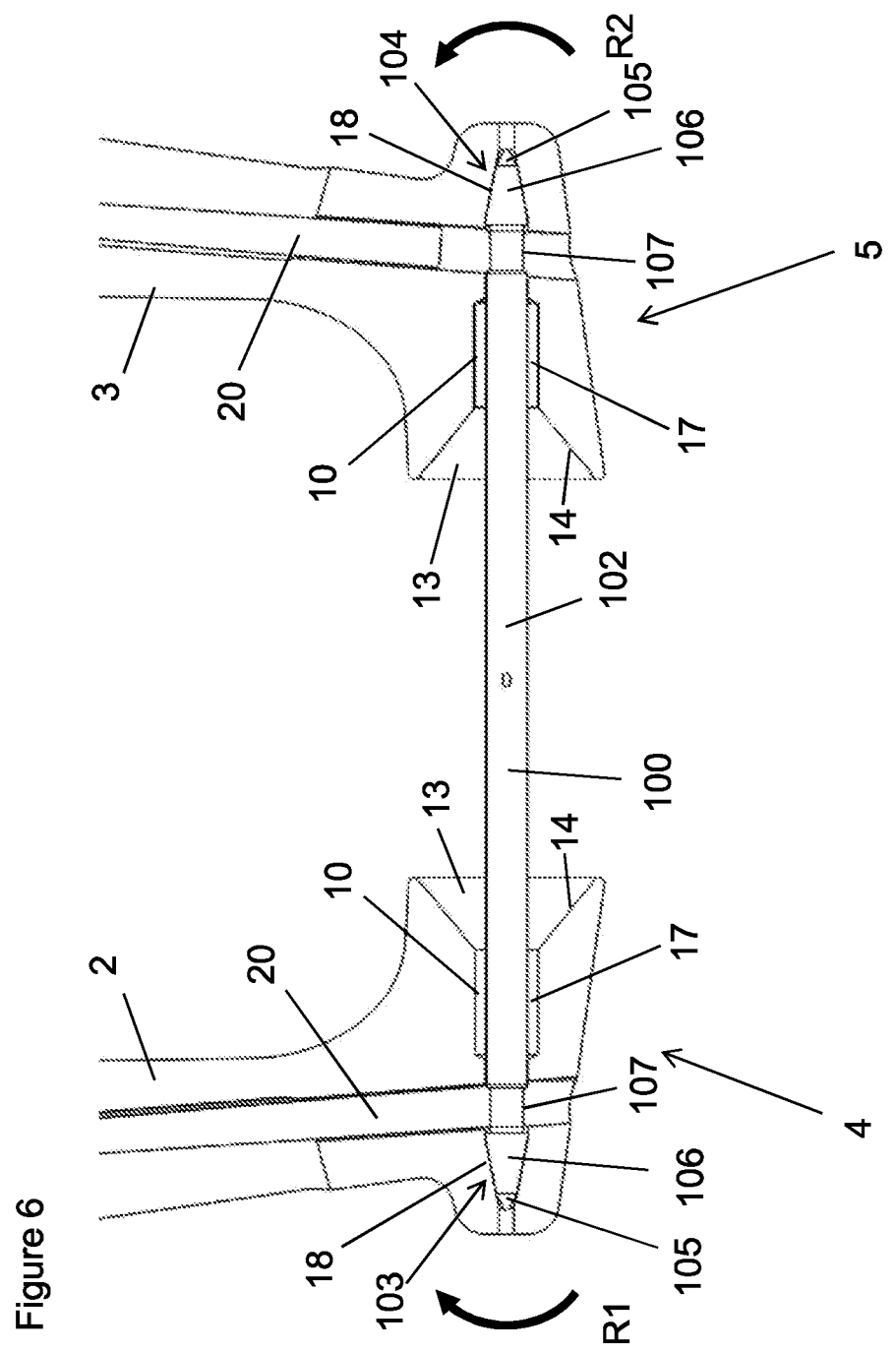
FIG. 6 shows the needle of FIGS. 3 and 4 arranged in the needle holders of the surgical suture apparatus of FIG. 1.

The needle end stop surface 106 is arranged to cooperate with a needle channel stop surface of a needle channel of a needle holder 4, 5 (see FIGS. 5 and 6). By providing a specific needle end stop surface 106 on the needle 100, separate from the needle point 105, to cooperate with the needle channel stop surface of a needle holder, the contact between the needle end stop surface 106 and the needle channel stop surface can be optimized for rotation of the first jaw element 2 and the second jaw element 3 about the respective needle ends 103, 104. This rotation is required for the activation movement of the operating device 8.

Since the needle end stop surface 106 is arranged to provide a contact between the needle 100 and the needle channel to facilitate rotation of the first jaw element 2 and the second jaw element 3 about the respective needle ends 103, 104, the needle point 105 is no longer needed to provide an engagement between the needle 100 and the associated needle channel. As a result, the needle point 105 of each of the first needle end 103 and the second needle end 104 may be optimized for piercing of tissue.

The circumferential locking groove 107 is a groove that extends over the whole circumference of the needle body 102. This locking groove 107 is provided to receive a needle locking element of a needle holder to lock the needle 100 in a needle channel of the needle holder 4, 5.

The needle body 102 has a diameter of about 0.4 mm. the needle body may also have any other suitable diameter. The total length of the needle 100 is for example approximately 10 mm. The length of the needle may be in the range of 7 mm to 12 mm. The needle 100 may be made of any suitable material, such as stainless steel.

Figure 4:
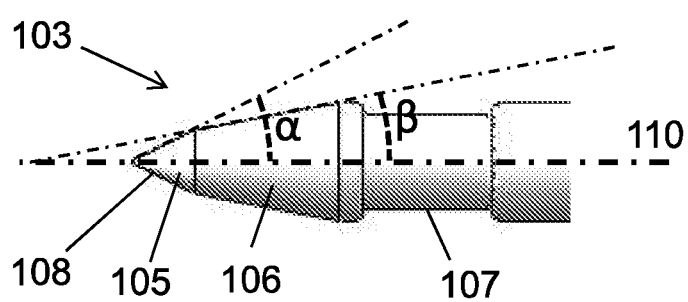
FIG. 4 shows a detail of the embodiment of the needle-suture combination of FIG. 3.

FIG. 4 shows the first needle end 103 in more detail. The second needle end 104 has the same construction and dimensions.

The needle point 105 comprises a substantially conical needle point surface extending at a first acute angle $\alpha$ with respect to a longitudinal axis 110 of the needle. The needle end stop surface 106 is also a substantially conical surface at a second acute angle $\beta$ with respect to the longitudinal axis 110 of the needle. The first acute angle $\alpha$ is larger than the second acute angle $\beta$. It is advantageous for rotation of the first jaw element 4 and the second jaw 5 about the first needle end 103 and the second needle end 104, when the needle end stop surface is more parallel to the longitudinal axis 110 of the needle than the needle point surface 108 of the needle point 105.

In the embodiment shown in FIGS. 3 and 4, the first acute angle $\alpha$ of the needle point surface is approximately 26 degrees with respect to the longitudinal axis 110 of the needle 100, and the second acute angle β of the conical surface of the needle end stop surface 106 is approximately 11 degrees with respect to the longitudinal axis 110 of the needle 100.

More generally, the first acute angle α may be in the range of 15 to 40 degrees with respect to the longitudinal axis 110 of the needle 100, for example in the range of 20 to 30 degrees with respect to the longitudinal axis 110 of the needle 100, and the second acute angle β of the needle end stop surface 106 may be in the range of 5 to 20 degrees with respect to the longitudinal 110 axis of the needle 100, for example in the range of 8 to 15 degrees with respect to the longitudinal axis 110 of the needle 100.

The first needle holder 4 and the second needle holder 5 of the surgical suture apparatus 1 of FIGS. 1 and 2 are designed to cooperate with the needle 100 shown in FIGS. 3 and 4.

FIG. 5 shows a cross section of the needle holder 4. The needle holder 4 comprises a needle channel 10 arranged to receive the first needle end 103 or the second needle end 104 of the needle 100. The needle channel 10 comprises an inlet 11 to introduce the first needle end 103 or the second needle end 104 into the needle channel 10.

At the inlet 11 of the needle channel 10 an alignment funnel 13 is arranged. This alignment funnel 13 is provided to align the needle 100 with the needle channel 10 when the needle 100 is introduced into the needle channel 10. The alignment funnel 13 comprises a funnel surface 14 at an acute funnel surface angle γ with respect to a longitudinal axis 15 of the needle channel 10. The acute funnel surface angle γ may be substantially the same as or smaller than the first acute angle α of the needle point surface of the needle point 10.

When the needle 100 is not perfectly aligned with the needle channel 10 when being introduced into the needle channel 10, i.e. when the longitudinal axis 110 of the needle does not correspond with the longitudinal axis 15 of the needle channel 10, the funnel surface 14 will guide the first needle end 103 or the second needle end 104 being pushed against this funnel surface 14 towards the needle channel 10. This guidance will ensure that the needle 100 will be properly aligned with the needle channel 10 to enter the needle channel 10. By making the acute funnel surface angle γ approximately the same or smaller than the first acute angle α of the needle, it is prevented that the needle point 105 of the needle 100 will pierce into the funnel surface 14 and prevent further movement of the first jaw element 2 and the second jaw element 3 to the take-over position, and/or will damage the funnel surface 14.

The wide end of the alignment funnel 13 for example has a cross section with a diameter of at least two times the needle diameter, for instance at least three times the needle diameter.

It is remarked that FIG. 2 shows a perspective view of the inlet 11 and the alignment funnel 13 of the second needle holder 5.

The needle channel 10 comprises a needle holding part 16 having a first diameter and a tissue receipt channel part 17 between the needle holding part 16 and the inlet 11 of the needle channel 10.

The tissue receipt channel part 17 has a second diameter larger than the first diameter of the needle holding part 16. In the shown embodiment, the first diameter of the needle holding part 16 is approximately 0.4 mm, i.e. about the same as the diameter of the needle 100, and the second diameter is approximately 0.6 mm. As a result, the second diameter is approximately 1.5 times the first diameter. The length of the tissue receipt channel part 17 is approximately 1 mm. Thus, the length of the tissue receipt channel part 17 is approximately 1.7 times the second diameter of the tissue receipt channel part 17. Since the second diameter is larger than the diameter of the needle 100, a circumferential space (see also FIG. 6) will be formed around the needle in the tissue receipt channel part 17, when the needle 100 is placed in the needle channel 10. This circumferential space can be used to receive tissue that is pulled into the needle channel 10 together with the needle 100. By providing the circumferential space, it is avoided that the needle 100 and/or the tissue is clamped or jammed in the needle channel. Clamping or jamming of the needle 100 may result in incorrect take-over of the needle 100. Clamping or jamming of tissue may lead to tissue damage when the surgeon pulls away the surgical suture apparatus 1 while the tissue is still held by the surgical suture apparatus 1.

It has been found that the above dimensions of the tissue receipt channel part 17 are suitable to receive tissue within the tissue receipt channel part 17 without being clamped or jammed in the needle channel 10, but also prevent further entry of tissue into the needle channel 10, in particular into the needle holding part 16. This ensures proper functioning of the suture apparatus 1 and avoids damage to tissue by inadvertently pulling tissue that is held by the respective needle holder 3, 4.

The needle holding part 16 of the needle channel 10 is configured to actually hold the needle 100. The needle holding part 16 comprises a needle channel stop surface 18 configure to cooperate with the needle end stop surface 106 of the needle 100. The needle channel stop surface 18 is a conical surface arranged at an acute angle θ with respect to the longitudinal axis of the needle channel 15 that substantially corresponds to the second acute angle β of the needle end stop surface 106. Thus, when the needle 100 is brought into the needle channel 10, the needle end stop surface 106 and the needle channel stop surface 18 will be placed against each other and cooperate with each other to form a bearing structure that allows some movement of the needle channel stop surface 18 with respect to the needle end stop surface 106 to facilitate rotational movement of the first jaw element 2 and the second jaw element 3 of the surgical suture apparatus 1 about the respective needle ends 103, 104.

The needle channel 10 further comprises a channel end part 19 that is arranged at the smaller side of the conical needle channel stop surface 18. The channel end part 19 is arranged to receive the needle point 105 when a needle 100 is introduced into the needle channel 10 such that the needle point will not come into contact with the wall of the needle channel 10, once arranged in the needle channel 10. This avoids that the shape or surface of the needle point 105 will get damaged due to pressures exerted by wall of the needle channel 10 on the needle 100. The channel end part 19 is an open ended channel, such that any tissue or debris that is pushed by the needle 100 into the channel end part 19 can be discharged through the open end of the channel end part 19.

The needle holder 4 further comprises a needle locking element 20 arranged in a needle locking element channel 21. The needle locking element 20 is movable between a non-locking position, as shown in FIG. 5, and a locking position, in which the needle locking element 20 is moved into the needle channel 10 such that the needle locking element 20 is placed in the locking groove 107 of the needle 100, when a needle 100 is arranged in the needle channel 10. The movement of the needle locking element 20 between the locking position and the non-locking position is operated by the operating device 8, as known in the art. It is remarked that the needle locking element channel 21 is also an open ended channel such that tissue and debris present in the needle channel 10 can also be discharged through the open end of the needle locking element channel 21.

FIG. 6 shows the first jaw element 2 and the second jaw element 3 in the take-over position, whereby the needle 100 is arranged with the first needle end 103 in the needle channel 10 of the first needle holder 4, and with the second needle end 104 in the needle channel 10 of a second needle holder 5.

The needle end stop surface 106 of each respective needle end 103, 104 is arranged against the needle channel stop surface 18 of each needle channel 10. As a result, the first needle holder 4 cannot be moved further towards the second needle holder 5. The needle locking element 20 of the first needle holder 4 is in the locking position, in which the needle locking element 20 extends into the needle locking groove 107 of the first needle end 103. The needle locking element 20 of the second needle holder 5 is in the non-locking position, in which the needle locking element 20 does not extend into the needle locking groove 107 of the second needle end 104.

To pass the needle 100 from the first needle holder 4 to the second needle holder 5, the operating device 8 should be activated such that the needle locking element 20 of the first needle holder 4 is moved to the non-locking position, while the needle locking element 20 of the second needle holder 5 is moved to the locking position.

As explained above, to activate the operating device 8, the first operating surface 29 on the first jaw element 3 and the second operating surface 30 on the second jaw element 4 should be moved towards each other. Since the first needle holder 4 and the second holder 5 cannot be moved towards each other due to the presence of the needle 100, the movement of the first operating surface 29 and the second operating surface 30 towards each other results in rotation R1 of the first jaw element 2 about the first needle end 103 and rotation R2 of the second jaw element 3 about the second needle end 104.

During the rotation R1, the needle end stop surface 106 of the first needle end 103 and the needle channel stop surface 18 of the first needle holder 4 cooperate with each other to form a bearing structure to facilitate rotational movement of the first jaw element 3 about the first needle end 103. Correspondingly, during the rotation R2, the needle end stop surface 106 of the second needle end 104 and the needle channel stop surface 18 of the second needle holder 5 cooperate with each other to form a bearing structure to facilitate rotational movement of the second jaw element 4 about the second needle end 104. The needle points 105 remain unaffected by these rotations R1, R2.

Further, it is remarked that by providing a straight needle 100 and circumferential locking grooves 107, the needle 100 can properly be arranged in the needle channels 10, independent of the rotational position of the needle 100 about its longitudinal axis 110. This is advantageous, as it is no longer required to align the rotational position of the needle 100 with respect to the needle channel 10 before loading the needle 100 into the respective needle holder 4, 5.

Figure 7:
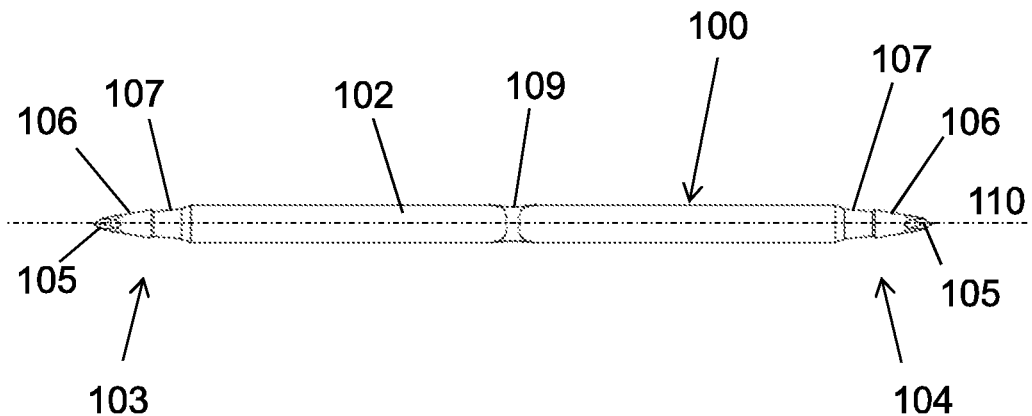
FIGS. 7, 8 and 9 show a second embodiment of a needle to be used in a needle-suture combination according to an embodiment of the invention.
Figure 8:
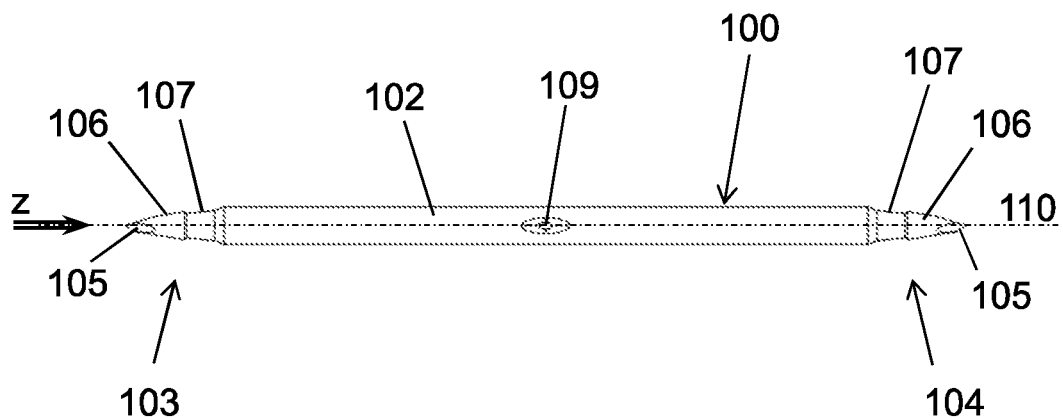
Figure 9:
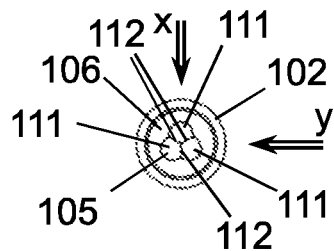

FIGS. 7, 8 and 9 show a second embodiment of a needle 100 to be used in a needle-suture combination according to an embodiment of the invention. FIGS. 7 and 8 show side views on the needle 100, as indicated in FIG. 9, in a first viewing direction x perpendicular to a longitudinal axis 110 of the needle 110 and a second viewing direction y perpendicular to the longitudinal axis 110 of the needle 110. The second viewing direction y of FIG. 8 is rotated 90 degrees with respect to the first viewing direction x of FIG. 7. FIG. 9 is a side view parallel to the longitudinal axis 110 of the needle 10 in the viewing direction z, indicated in FIG. 8.

The needle 100 is configured to be used in an embodiment of the surgical apparatus, as generally depicted in FIGS. 1 and 2. The first needle holder 4 and the second needle holder 5 may be adapted to the shape and dimensions of the needle 100 shown in FIGS. 7, 8 and 9.

The needle 100 comprises a straight needle body 102 having a first needle end 103 and a second needle end 104. Midway between the first needle end 103 and the second needle end 104, a through-going hole 109 is provided through which a connection loop of a suture may be arranged to connect a suture to the needle 100. The suture may for example be configured as the suture shown in FIG. 3, comprising the connection loop, a suture thread and a connector connecting the suture thread to the connection loop.

Corresponding to the embodiment of FIG. 4, each of the first needle end 103 and the second needle end 104 comprises a needle point 105, a needle end stop surface 106 and a circumferential locking groove 107.

The needle point 105 is a pointed end of the needle 100 that can be used to pierce tissue or other material through which the suture should be arranged.

The needle end stop surface 106 is arranged to cooperate with a needle channel stop surface of a needle channel of a needle holder 4, 5 (see FIGS. 5 and 6) similar to the embodiment of FIG. 4. The shape and dimensions needle channel stop surface may be adapted to the shape and dimensions of the needle end stop surface 106.

Since the needle end stop surface 106 is arranged to provide a contact between the needle 100 and the needle channel to facilitate rotation of the first jaw element 2 and the second jaw element 3 about the respective needle ends 103, 104, the needle point 105 is no longer needed to provide an engagement between the needle 100 and the associated needle channel. As a result, the needle point 105 of each of the first needle end 103 and the second needle end 104 may be optimized for piercing of tissue.

The circumferential locking groove 107 is a groove that extends over the whole circumference of the needle body 102. This locking groove 107 is provided to receive a needle locking element of a needle holder to lock the needle 100 in a needle channel of the needle holder 4, 5. The locking grooves 107 of the needle 100 of the embodiment of FIGS. 7, 8 and 9 have a conical base surface. The base surfaces of the locking grooves 107 taper in the direction of the through-going hole 109 radially outwards with respect to the longitudinal axis 110. The shapes of the needle locking elements 20 of the first needle holder 4 and the second needle holder 5 may be adapted to this shape of the locking grooves 107. The angle of the base surface of the locking grooves 107 may for example be 2 to 15 degrees, for instance 4 to 10 degrees with respect to the longitudinal axis 110 of the needle 100. Such conical base surface of the locking groove may also be applied in any other embodiment of a needle, for example the embodiment shown in FIGS. 3 and 4.

The needle body 102 has a diameter of about 0.4 mm. The needle body may also have any other suitable diameter. The total length of the needle 100 is for example approximately 9 mm. The length of the needle is for example in the range of 7 mm to 12 mm. The needle 100 may be made of any suitable material, such as stainless steel.

Figure 10:
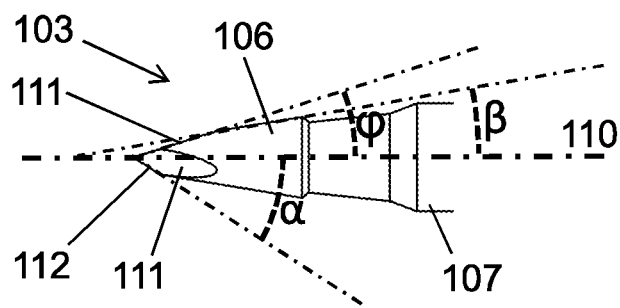
FIG. 10 shows the first needle end of the needle of FIGS. 7, 8 and 9 in more detail.

FIG. 10 shows the first needle end 103 of the needle 100 of FIGS. 7, 8 and 9 in more detail. The second needle end 104 has the same construction and dimensions.

In the embodiment of FIGS. 7, 8 and 9, the needle points 105 comprise a three facet needle point surface, formed by three facets 111 equally distributed over the circumference of the respective needle end 103, 104. The needle point surface is the surface defining the needle point. The three facets 111 may for example be machined in a needle having two conical surfaces as the embodiment shown in FIGS. 3 and 4.

The three facets 111 are each arranged at a facet angle φ with respect to the longitudinal axis 110 of the needle. The facets 111 define three needle point edges 112 arranged at a first acute angle α with respect to the longitudinal axis 110 of the needle.

The needle end stop surface 106 is a substantially conical surface at a second acute angle β with respect to the longitudinal axis 110 of the needle. The first acute angle α and the facet angle φ are each larger than the second acute angle β.

In the embodiment shown in FIGS. 7, 8 and 9, the facet angle φ is approximately 17.5 degrees and the first acute angle α is approximately 30 degrees with respect to the longitudinal axis 110 of the needle 100. The second acute angle β of the conical surface of the needle end stop surface 106 is approximately 9.4 degrees with respect to the longitudinal axis 110 of the needle 100.

More generally, the facet angle φ and the first acute angle α may for example be in the range of 15 to 40 degrees with respect to the longitudinal axis 110 of the needle 100 and the second acute angle β of the needle end stop surface 106 may be in the range of 5 to 20 degrees with respect to the longitudinal 110 axis of the needle 100, for example in the range of 8 to 13 degrees with respect to the longitudinal axis 110 of the needle 100.

The invention claimed is:

1. A needle holder to hold a needle-suture combination that comprises a needle having a first needle end and a second needle end opposite to the first needle end and a suture connected to the needle between the first needle end and the second needle end, wherein the first needle end and the second needle end each comprise a needle point, a locking groove and a needle end stop surface between the locking groove and the needle point, wherein the needle holder comprises:
a needle channel arranged to receive the first needle end or the second needle end, the needle channel comprising an inlet to introduce the respective needle end into the needle channel, and
a needle locking element to be received in the locking groove of the respective needle end to lock the respective needle end in the needle channel,
wherein the needle channel comprises a needle channel stop surface to cooperate with the needle end stop surface of the respective needle end of the needle-suture combination,
wherein the needle channel comprises a needle holding part having a first diameter and in which the needle channel stop surface is provided, and a tissue receipt channel part between the needle holding part and the inlet of the needle channel, the tissue receipt channel part having a second diameter in the range of 1.2 to 2.5 times the first diameter, and
wherein the needle channel comprises at the inlet an alignment funnel to align the needle end with the needle channel.

2. The needle holder of claim 1, wherein the needle channel stop surface is substantially conical.

3. The needle holder of claim 1, wherein the needle channel is configured to be free of contact of the needle point when the needle channel stop surface engages the needle end stop surface.

4. The needle holder of claim 1, wherein the alignment funnel comprises a funnel surface at an acute funnel surface angle with respect to a longitudinal axis of the needle channel, wherein the acute funnel surface angle is substantially the same as or smaller than 40 degrees.

5. The needle holder of claim 1, wherein a length of the tissue receipt channel part is from at least 1 times the second diameter to 1.5 times the second diameter.

6. The needle holder of claim 1, wherein the second diameter is in the range of 1.3 to 1.8 times the first diameter.

7. A surgical suture apparatus for passing a double-ended surgical needle-suture combination forwards and backwards, wherein the surgical apparatus comprises:
a first jaw element, comprising a first needle holder configured as the needle holder of claim 1 to hold a first needle end of the needle,
a second jaw element comprising a second needle holder configured as the needle holder of claim 1 to hold a second needle end of the needle, and
an operating device to operate the first needle holder and the second needle holder to alternately hold the first needle end by the first needle holder and the second needle end by the second needle holder.

8. A needle holder to hold a needle-suture combination, wherein the needle holder comprises:
a needle channel arranged to receive a needle end of a needle of the needle-suture combination, the needle channel comprising:
an inlet to introduce the respective needle end into the needle channel,
a needle holding part having a first diameter, and
a tissue receipt channel part between the needle holding part and the inlet of the needle channel, the tissue receipt channel part having a second diameter in the range of 1.2 to 2.5 times the first diameter,
wherein the needle channel comprises at the inlet an alignment funnel to align the needle end with the needle channel.

9. The needle holder of claim 8, wherein the alignment funnel comprises a funnel surface at an acute funnel surface angle with respect to a longitudinal axis of the needle channel, wherein the acute funnel surface angle is the same as or smaller than 40 degrees.

10. The needle holder of claim 8, wherein the second diameter is in the range of 1.3 to 1.8 times the first diameter.

11. The needle holder of claim 10, wherein the first diameter of the needle holding part is approximately 0.4 mm and the second diameter is approximately 0.6 mm.

12. A needle holder to hold a needle-suture combination, wherein the needle holder comprises:
a needle channel arranged to receive a needle end of a needle of the needle-suture combination, the needle channel comprising:
an inlet to introduce the respective needle end into the needle channel,
a needle holding part having a first diameter, and
a tissue receipt channel part between the needle holding part and the inlet of the needle channel, the tissue receipt channel part having a second diameter in the range of 1.2 to 2.5 times the first diameter, and wherein a length of the tissue receipt channel part is at least 1 times the second diameter.

\* \* \* \* \*